United States Patent
Kim et al.

(10) Patent No.: US 7,282,028 B2
(45) Date of Patent: Oct. 16, 2007

(54) METHOD AND APPARATUS FOR MEASURING ANIMAL'S CONDITION BY ACQUIRING AND ANALYZING ITS BIOLOGICAL SIGNALS

(75) Inventors: Kyung-hwan Kim, Seongnam (KR); Seok-won Bang, Seoul (KR); Hyoung-ku Lee, Suwon (KR)

(73) Assignee: Samsung Electronics Co., Ltd., Suwon, Kyungki-Do (KR)

( * ) Notice: Subject to any disclaimer, the term of this patent is extended or adjusted under 35 U.S.C. 154(b) by 812 days.

(21) Appl. No.: 10/339,461

(22) Filed: Jan. 10, 2003

(65) Prior Publication Data
US 2003/0166996 A1 Sep. 4, 2003

(30) Foreign Application Priority Data
Jan. 11, 2002 (KR) .................................. 2002-1696

(51) Int. Cl.
*A61B 5/00* (2006.01)
(52) U.S. Cl. ....................................... 600/300; 128/920
(58) Field of Classification Search ........ 600/300–301; 128/903–905; 340/439
See application file for complete search history.

(56) References Cited

U.S. PATENT DOCUMENTS

| | | | |
|---|---|---|---|
| 5,046,453 A | | 9/1991 | Vinci |
| 5,054,428 A | | 10/1991 | Farkus |
| 5,818,354 A | * | 10/1998 | Gentry .................. 340/870.16 |
| 5,835,008 A | * | 11/1998 | Colemere, Jr. ............... 340/439 |
| 6,599,243 B2 | * | 7/2003 | Woltermann et al. ........ 600/300 |

FOREIGN PATENT DOCUMENTS

JP 10-3479 A 1/1998

(Continued)

OTHER PUBLICATIONS

Vapnik, V., An Overview of Statistical Learning Theory, IEEE Transactions on Neural Networks, vol. 10, No. 5, Sep. 1999, pp. 988-999.

(Continued)

*Primary Examiner*—Max F. Hindenburg
*Assistant Examiner*—Michael C Astorino
(74) *Attorney, Agent, or Firm*—Buchanan Ingersoll & Rooney PC

(57) ABSTRACT

A method and apparatus for measuring the biological condition of an animal by acquiring and analyzing its biological signals are provided. The biological signals from skin temperature, a photoplenthysmogram (PPG), an electrocardiogram (ECG), electrodermal activity (EDA), an electromyogram (EMG), and an electrogastrogram (EGG) are detected using a biological signal detection unit which is attached to the animal's skin. Feature vectors, including the mean heart rate of the photoplenthysmogram and its standard deviation, the very low frequency, low frequency, and high frequency components of heart rate variability, the frequency and mean amplitude of skin conductance responses, and the mean and maximum skin temperatures, are extracted from the detected biological signals. The biological condition, including needs and emotions, of the animal as to whether or not the animal feels hunger or fear, how much the animal is stressed, or whether or not the animal needs to have a bowel movement, is determined using a pattern classifier which has learned reference vectors, which reflect the behaviors, needs, and emotions of different kinds of animals for various biological conditions and are stored in a predetermined database. Therefore, the biological condition of the animal can be determined through instrumental communication, not through human languages, and the breeding of pets can be efficiently managed.

20 Claims, 20 Drawing Sheets

FOREIGN PATENT DOCUMENTS

JP  2001-28961 A  2/2001
KR  10-0357250 B1  10/2002

OTHER PUBLICATIONS

Kim, K. et al., *Neural Spike Sorting Under Nearly 0-dB Signal-to-Noise Ratio Using Nonlinear Energy Operator and Artificial Neural-Network Classifier*, IEEE Transaction Son Biomedical Engineering, vol. 47, No. 10, Oct. 2000, pp. 1406-1411.

Berger, R., *An Efficient Algorithm for Spectral Analysis of Heart Rate Variability*, IEEE Transactions on Biomedical Engineering, vol. BME-33, No. 9, Sep. 1986, pp. 900-904.

Hyvarinen, A., *What is Independent Component Analysis?*, Wiley, 2001, pp. 147-164.

Chen, J. et al., *Spectral Analysis of Episodic Rhythmic Variations in the Cutaneous Electrogastrogram*, IEEE Transactions on Biomedical Engineering, vol. 40, No. 2, Feb. 1993, pp. 128-135.

Duda, R., et al., *Pattern Classification*, 2$^{nd}$ Ed., Wiley, 2000, pp. 23, 117-124.

Webster, J., et al., *Medical Instrumentation*, 1999, pp. 450-452.

Hayes, M., *Statistical Digital Signal Processing and Modeling*, Wiley, 1996, pp. 194, 411.

Notice to Submit Response issued by the Korean Patent Office on Mar. 19, 2004 in corresponding application 10-2002-0001696.

* cited by examiner

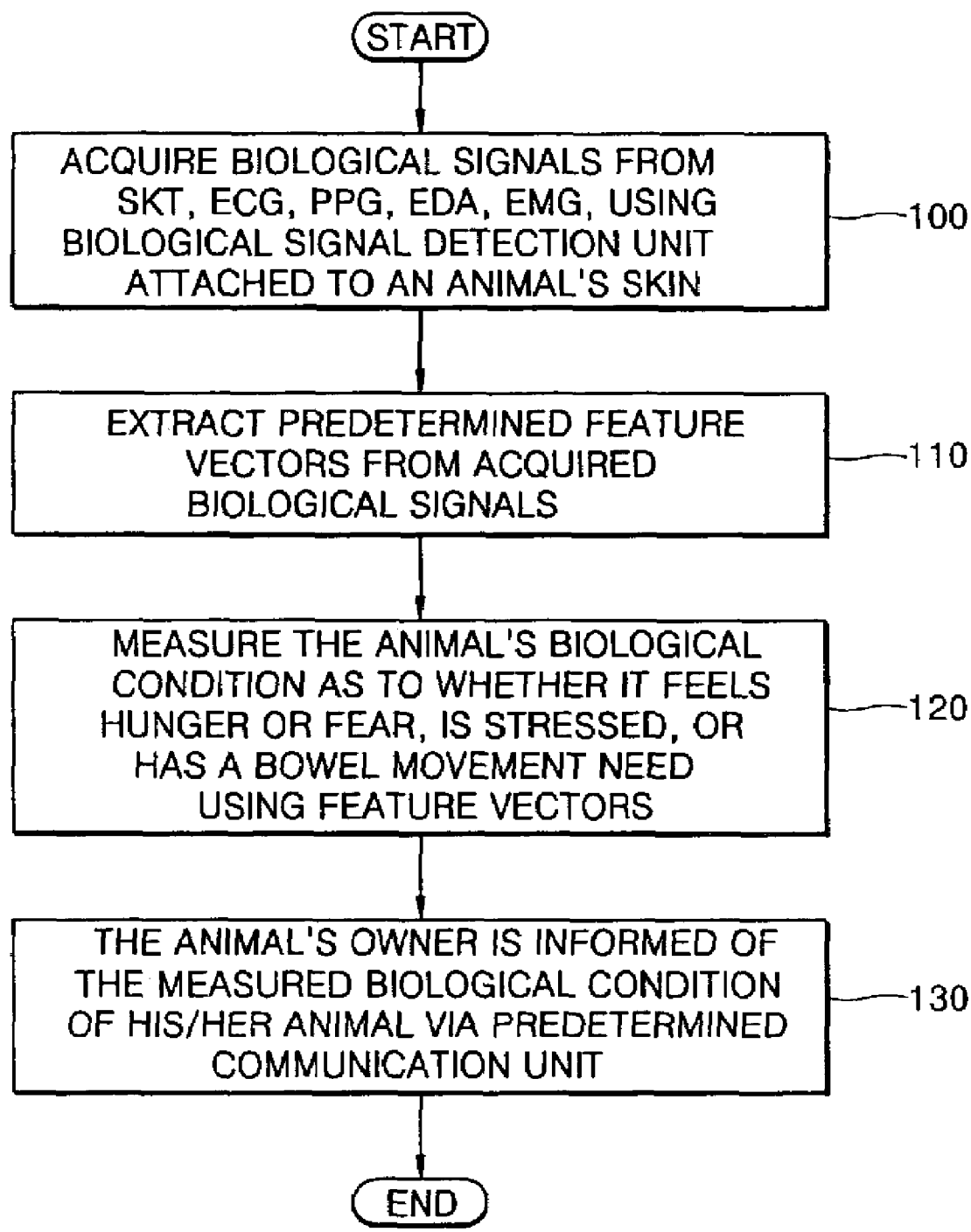

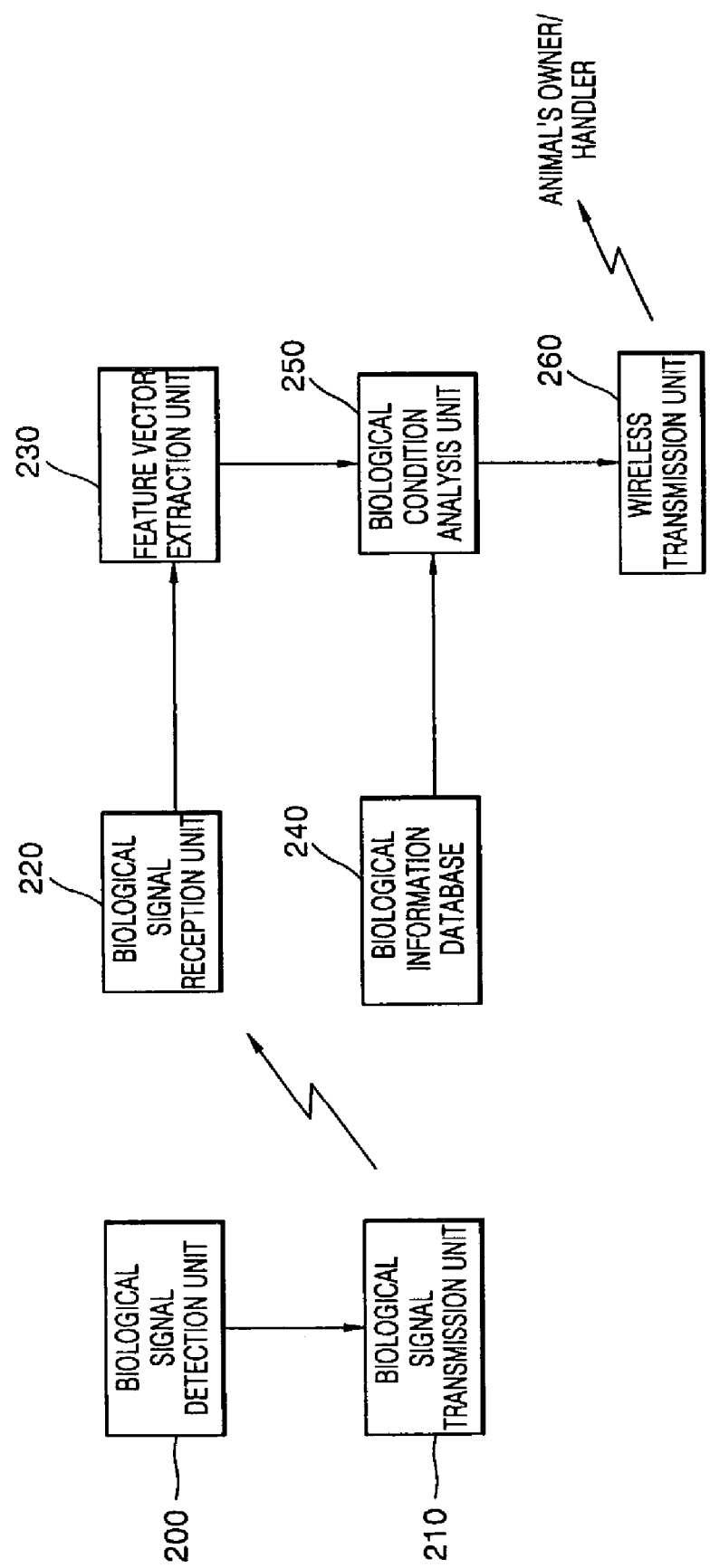

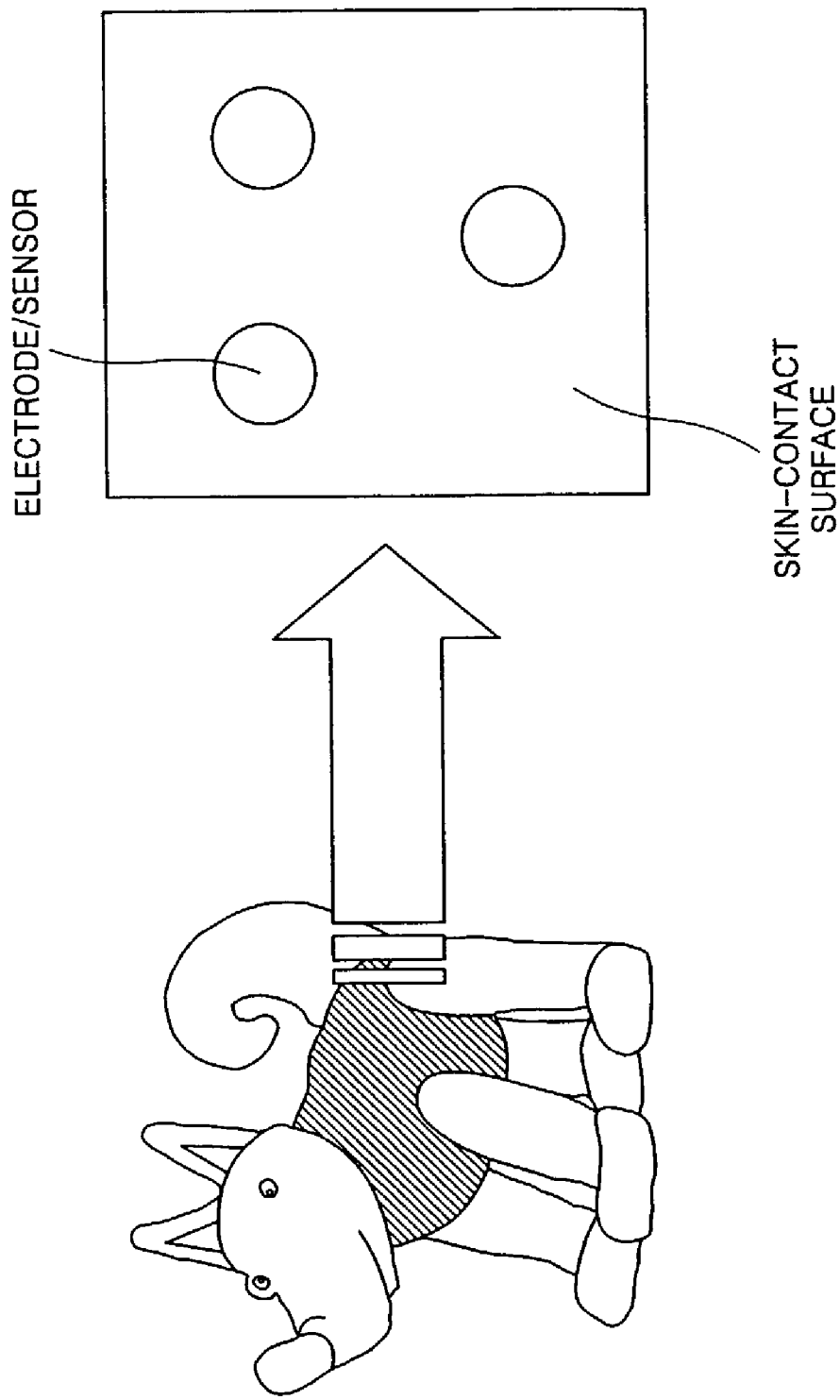

METHOD AND APPARATUS FOR MEASURING ANIMAL'S CONDITION BY ACQUIRING AND ANALYZING ITS BIOLOGICAL SIGNALS

This application claims priority from Korean Patent Application No. 2002-1696, filed Jan. 11, 2002 in the Korean Industrial Property Office, which is incorporated herein in its entirety by reference.

BACKGROUND OF THE DISCLOSURE

1. Field of the Disclosure

The present disclosure relates to processing a biological signal, and more particularly, to a method and apparatus for measuring an animal's emotional condition and needs by acquiring and analyzing biological signals of an animal, which enable non-human animal-to-human communications.

2. Description of the Related Art

The breeding of pets continues to increase worldwide. Reportedly, about two million pets are bred in South Korea alone, forming a two hundred billion won pet related market.

Since it is absolutely impossible to communicate with animals using human languages, pet owners yearn to know the mental and physical condition of his/her pet(s). Attempts have been made to measure the physical and emotional condition of pets, but no progress has been made.

Korean Patent Application No. 2000-41437 discloses a remote pet breeding method via the Internet. In the disclosure, a pet is remotely monitored via the Internet and is fed by clicking on an instruction with a mouse. However, the disclosure is far removed from the measurement of the pet's physical and emotional state.

Japanese Laid-open Patent Application No. 2001-28961 discloses a pet monitoring and feeding system to be used when the pet's owner is away. According to the disclosure, the location of a pet can be traced by attaching an RF tag to the pet, and the point of time for feeding and giving water the pet is controlled by a timer. However, this disclosure seems to be unrelated to informing the pet owner of the state of his/her pet.

Japanese Laid-open Patent Application No. 1998-3479 discloses an animal's intention translation method. An animal's sound or motion is transmitted to an animal's intention interpretative system and compared with previously stored reference data. A reference data corresponding to the animal's sound or motion is selected, and the animal's intention is translated based on the selected data in a human language so as to inform the owner of his/her animal's intention. However, the disclosure is not fully described such as to implement the method, for example, how to interpret the animal's sound and how to read the animal's intention from an image signal of an animal's motion. Accordingly, it seems impossible to understand the animal's intention or emotional state using the disclosed method.

U.S. Pat. No. 5,046,453 discloses an animal training apparatus. According to the disclosure, when a dog barks or does not behave in a trained way, a command signal is wirelessly transmitted to a receiver attached to its collar, in order to flow a cold fluid so as to stop the unexpected behavior of the dog. U.S. Pat. No. 5,054,428 discloses a method and apparatus for remote conditioned cue control of animal training stimulus. In the disclosure, when a trained dog behaves in an unexpected way, an electrical stimulus signal is applied to the dog for a short duration to call the dog's attention, and the intensity of the electrical stimulus signal is gradually increased when calling the dog's attention is unsuccessful. However, both U.S. applications described above seem to be unrelated to understanding the mental and physical state of animals.

PCT Patent Publication No. WO99/42968 discloses a pet locator system, which controls the location of a movable object, such as a pet, and informs a user when the movable object does not reach a specific place on time. PCT Patent Publication No. 96/30882 discloses a wireless pet containment system for keeping a pet within a space using a wireless transceiver. These two disclosures are not related to understanding the physical and mental state of animals.

As described above, conventionally, owners of trainers of pets of animals cannot be aware of the physical or mental state of the pets or animals, which cannot communicate with people using human languages.

SUMMARY OF THE DISCLOSURE

Accordingly, the disclosure provides a method and apparatus for measuring animal's biological condition by acquiring and analyzing its biological signals.

In one aspect, the disclosure provides a method for determining the biological condition of an animal by acquiring and analyzing a biological signal, the method comprising: (a) acquiring a predetermined biological signal using a biological signal detection unit which is attached to the animal; (b) extracting a predetermined feature vector from the acquired predetermined biological signal; and (c) analyzing and determining the biological condition of the animal, including emotions and needs of the animal, from the predetermined feature vector.

In another aspect, the disclosure provides a method for determining the biological condition of an animal by acquiring and analyzing biological signals, the method comprising: (a) acquiring biological signals from skin temperature, a photoplethysmogram (PPG), an electrocardiogram (ECG), electrodermal activity (EDA), an electromyogram (EMG), and an electrogastrogram (EGG) using a biological signal detection unit which is attached to the animal's skin; (b) extracting feature vectors from the acquired biological signals, the feature vectors including the mean heart rate of the photoplethysmogram and its standard deviation, the very low frequency, low frequency, and high frequency components of heart rate variability, the frequency and mean amplitude of skin conductance responses which are obtainable from the electroderminal activity, and the mean and maximum skin temperatures; and (c) analyzing and determining the biological condition, including needs and emotions, of the animal as to whether or not the animal feels hunger or fear, how much the animal is stressed, or whether or not the animal needs to have a bowel movement, using a support vector machine which has learned reference vectors, which reflect the behaviors, needs, and emotions of different kinds of animals for various biological conditions and are stored in a predetermined database.

In another aspect, the disclosure provides an apparatus for measuring the biological condition of an animal by acquiring and analysing biological signals, the apparatus comprising: a biological signal detection unit which is attached to the animal's skin and detects a biological signal of the animal; and a condition analysis unit which determines the biological condition, including needs and emotions, of the animal using a predetermined feature vector extracted by analysing the biological signal detected by the biological signal detection unit.

In another aspect, the disclosure provides an apparatus for measuring the biological condition of an animal by acquiring and analysing biological signals, the apparatus comprising: a biological signal detection unit including a plurality of sensors and electrodes, which is attached to the animal's skin and detects biological signals from skin temperature, an electrocardiogram (ECG), a photoplethysmogram (PPG), electrodermal activity (EDA), an electromyogram (EMG), and an electrogastrogram (EGG); a feature vector extraction unit which extracts feature vectors from the biological signals detected by the biological signal detection unit, the feature vectors including the mean heart rate of the photoplethysmogram and its standard deviation, the very low frequency, low frequency, and high frequency components of heart rate variability, the frequency and mean amplitude of skin conductance responses, and the mean and maximum skin temperatures; a biological information database which stores reference vectors reflecting the behaviors, needs, and emotions of different kinds of animals for various biological conditions; and a biological condition analysis unit which compares the feature vectors extracted by the feature vector extraction unit with reference vectors of the biological information database and determines the biological condition, including needs and emotions, of the animal as to whether or not the animal feels hunger or fear, how much the animal is stressed, or whether or not the animal needs to have a bowel movement.

BRIEF DESCRIPTION OF THE DRAWINGS

The above features and advantages of the present disclosure will become more apparent by describing in detail exemplary embodiments thereof with reference to the attached drawings in which:

FIG. 1 is a flowchart of a method for measuring the biological condition of an animal by acquiring and analysing its biological signals, according to the present disclosure;

FIG. 2 is a block diagram of an apparatus for performing the method of FIG. 1 for measuring the biological condition of an animal by acquiring and analysing its biological signals;

FIGS. 3A and 3B show a collar type sensor module and a wearable sensor module, respectively, attached to the animal as a biological signal detection unit according to the present disclosure;

DETAILED DESCRIPTION OF THE DISCLOSURE

Figure 3A:
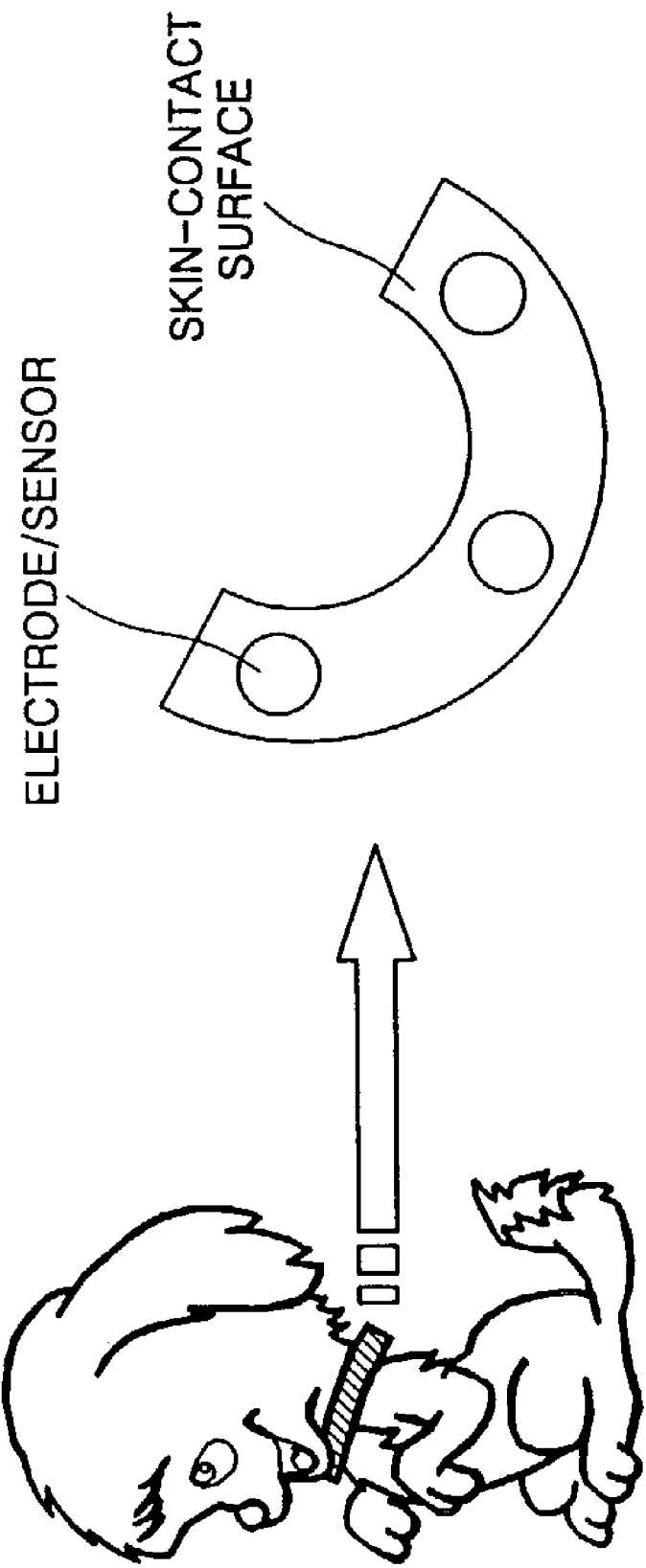

FIG. 1 is a flowchart for illustrating a method for measuring the biological condition of an animal by acquiring and analysing its biological signals, according to the present disclosure. Biological signals of an animal are acquired by determining the animal's skin temperature (SKT), electrocardiogram (ECG) reading, photoplethysmogram (PPG) reading, electrodermal activity (EDA), electromyogram (EMG) reading, and electrogastrogram (EGG) reading using a biological signal detection unit attached to the animal's skin, and the acquired biological signals are transmitted (step 100). The transmitted biological signals are received, and predetermined feature vectors are extracted from the received biological signals (step 110). Next, the biological condition of the animal, as to whether it feels hunger or fear, how much it is stressed, or whether or not it has a bowel movement need, is measured in step 120 using the feature vectors. Reference vectors which reflect the behaviors, needs, and emotions of different kinds of animals for various biological conditions and which previously stored in a predetermined database are compared with the extracted feature vectors in order to measure the animal's biological condition as to whether it feels hungry or fear, how much it is stressed, or whether or not it has a bowel movement need.

Next, the animal's owner is informed of the measured biological condition of his/her animal via a predetermined communication unit in step 130.

When the animal's owner wishes to provide an expert, such as a veterinarian, with the information on the biological condition of his/her animal, the biological signals obtained in step 100 or the biological condition measured in step 120 are transmitted to the expert via a predetermined communication unit, such as a wireless communication unit. In this case, it is preferable that the animal's owner be informed of the result of a diagnosis performed by the expert based on the biological signals and the measured biological condition via a predetermined communication unit.

FIG. 2 is a block diagram of an apparatus for performing the method of FIG. 1 for measuring the biological condition of an animal by acquiring and analyzing its biological signals. The apparatus of FIG. 2 includes a biological signal detection unit 200 including a plurality of sensors and electrodes, which is attached to the animal's skin so as to detect the animal's biological signals, a biological signal transmission unit 210 which wirelessly transmits the biological signals, as detected by the biological signal detection unit 200, using a predetermined method, a biological signal reception unit 220 which receives the transmitted biological signals, and a feature vector extraction unit 230 which extracts feature vectors indicative of the animal's biological condition, including the mean heart rate and its standard deviation, the very low frequency (VLF), low frequency (LF), and high frequency (HF) components of the ECG, the frequency and mean amplitude of skin conductance responses, and the mean and maximum skin temperatures. The apparatus of FIG. 2 includes a biological information database 240 which stores reference vectors, which reflect the behaviors, needs, and emotions of different kinds of animals for various biological conditions, and a biological condition analysis unit 250 which analyzes the animal's biological condition as to whether it feels hunger or fear, how much it is stressed, or whether or not it has a bowel movement need, by comparing the feature vectors extracted by the feature vector extraction unit 230 with the reference vectors.

Preferably, the biological condition measuring apparatus of FIG. 2 further includes a wireless transmission unit 260 which wirelessly transmits the biological condition of the animal, as measured by the biological condition analysis unit 250, to the owner of the animal.

The biological signals detected by the biological signal detection unit 200 or the animal's biological condition measured by the biological condition analysis unit 250 can be transmitted to an expert, such as a veterinarian, via the wireless transmission unit 260, for diagnostic purposes.

Embodiments of the present disclosure will be described in detail based on the method of FIG. 1 and the structure of FIG. 2.

Human beings communicate with one another mostly through dialogues. Accordingly, new technologies of human-computer interaction (HCI) for conveying human intentions to artificial electronic systems, such as computers or robots, have been developed based on voice-related techniques, such as speed recognition and voice synthesis.

Human beings have also communicated partially with pets, such as dogs or cats, which are on intimate terms with their owners, from his/her pet's groans or particular gestures.

According to the present disclosure, biological signals which reflect a pet's needs and emotional condition are detected using a sensor module attached to the animal's skin as the biological logical condition detection unit and are wirelessly transmitted so as to be processed by a processor using a predetermined signal processing method and pattern recognition, so that the physical and mental conditions of the pet can be measured. Next, information on the pet's physical and mental conditions is transferred to an expert, such as a veterinarian.

Like human beings, a non-human animals' emotional condition affects its autonomic nervous system (sympathetic and parasympathetic nervous systems), and thus biological signals reflect the condition of the autonomic nervous system, i.e., related to heart rate variability, electrodermal activity, skin temperature, etc. Also, an animal's need for a bowel movement or its feeling of hunger can be reflected in the biological signals of the EMG and EGG. By continuously detecting appropriate biological signals among various biological signals, which indicate the biological condition of the animal, and appropriately processing and interpreting the detected biological signals, information on the animal's emotional condition or its needs can be extrapolated.

FIGS. 3A and 3B illustrate examples of the sensor module attached to animals and serving as the biological signal detection unit according to the present disclosure. FIG. 3A shows a collar type sensor module, and FIG. 3B shows a wearable sensor module. Sensors and electrodes are attached to the inner surface of the sensor module to contact the animal's skin.

It is preferable that the sensor module serving as the biological signal detection unit 200 be configured to continuously detect biological signals of the pet without discomforting the pet. To this end, the sensor module can be implemented as a collar type or a wearable type, as shown in FIGS. 3A and 3B, respectively, with electrodes and sensors attached on a rigid support. In this case, the electrodes and sensors must directly contact the skin of the neck or abdomen of the animal.

Biological signals are acquired from the SKT, ECG, PPG, EDA, EMG, and EGG using the sensors/electrodes of the biological signal detection unit 200 attached to the animal's skin (Step 100). The acquired biological signals are processed by a preamplifier, a filter, a main amplifier, etc, subjected to time divisional multiplexing, analog-to-digital conversion, and modulation, and wirelessly transmitted via an RF transmitter. Those processes are performed in the biological signal transmission unit 210.

The biological signal reception unit 220 receives the biological signals transmitted from the biological signal transmission unit 210 via an RF receiver and restores the original biological signals through a series of processes, such as demodulation, signal recovery, etc. The restored biological signals can be analog signals which are detected by the biological signal detection unit 200 or digital signals. However, it is preferable that the restored biological signals be digital signals in the following case.

The restored biological signals are transmitted to the feature vector extraction unit 230 so as to extract feature vectors indicating the biological condition of the animal. The feature vector extraction unit 230 can be implemented using hardware, for example, as an add-on card, in a computer system. Alternatively, the feature vector extraction unit 230 can be implemented in hardware, such as a computer system, using software.

Hereinafter, the operation and function of the feature vector extraction unit 230 will be described. When the sympathetic or parasympathetic nervous systems of the animal are stimulated due to an emotional change, the stimulation is transferred to the sinoatrial (SA) node acting as a cardiac pacemaker and varies the heart rate in a particular pattern. The heart rate pattern varies with emotional changes. The heart rate of pets can be measured by a variety of methods, for example, by electrocardiography (ECG), phonocardiography, photolethysmography (PPG), etc.

When a collar type sensor module as shown in FIG. 3A is used as the biological signal detection unit 200, a PPG is measured from the caroticum, and the heart rate is measured using the alternating current (AC) signal of the PPG. As a result, heart rate variability can be measured. A method for constructing a photolethysmographic sensor module is described in "Medical Instrumentation" (J. G. Webster, 1999).

Alternatively, when a sensor module as shown in FIG. 3B is used, an ECG can be obtained using a two-electrode or three-electrode method.

Figure 4A:
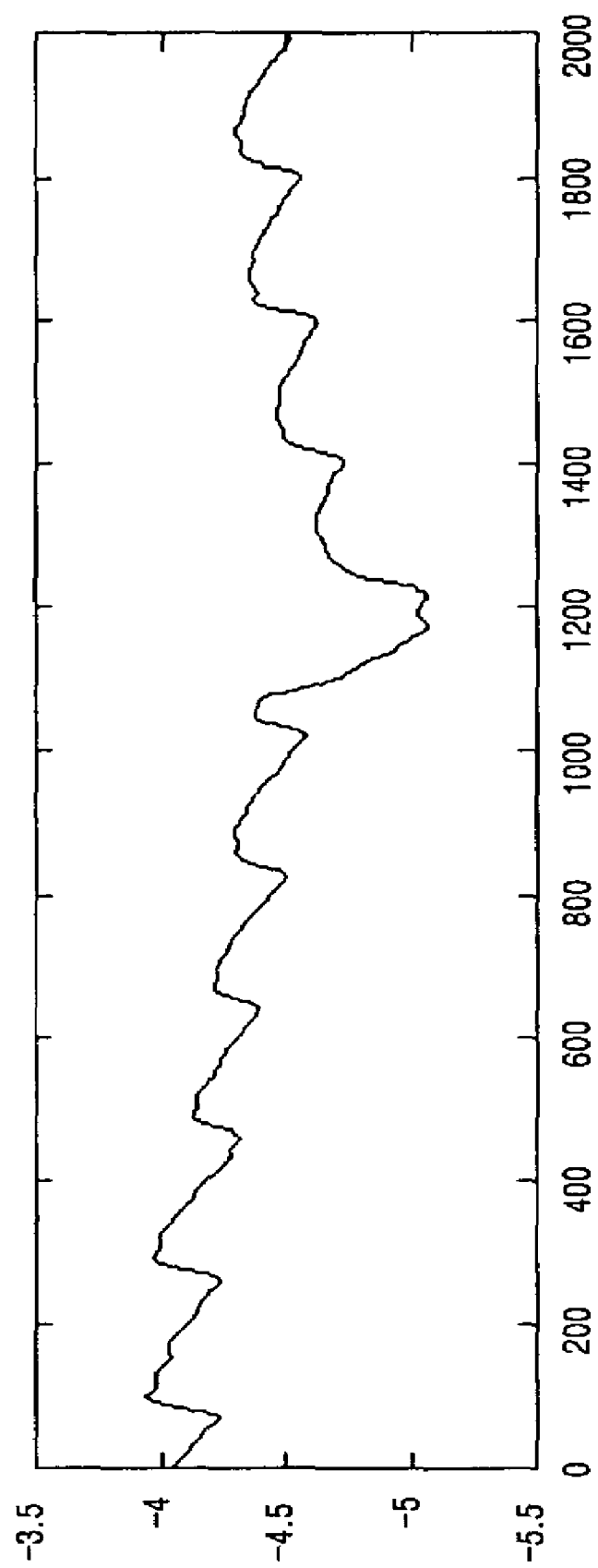
FIG. 4A shows an example of a photoplenthysmogram (PPG)
Figure 4B:
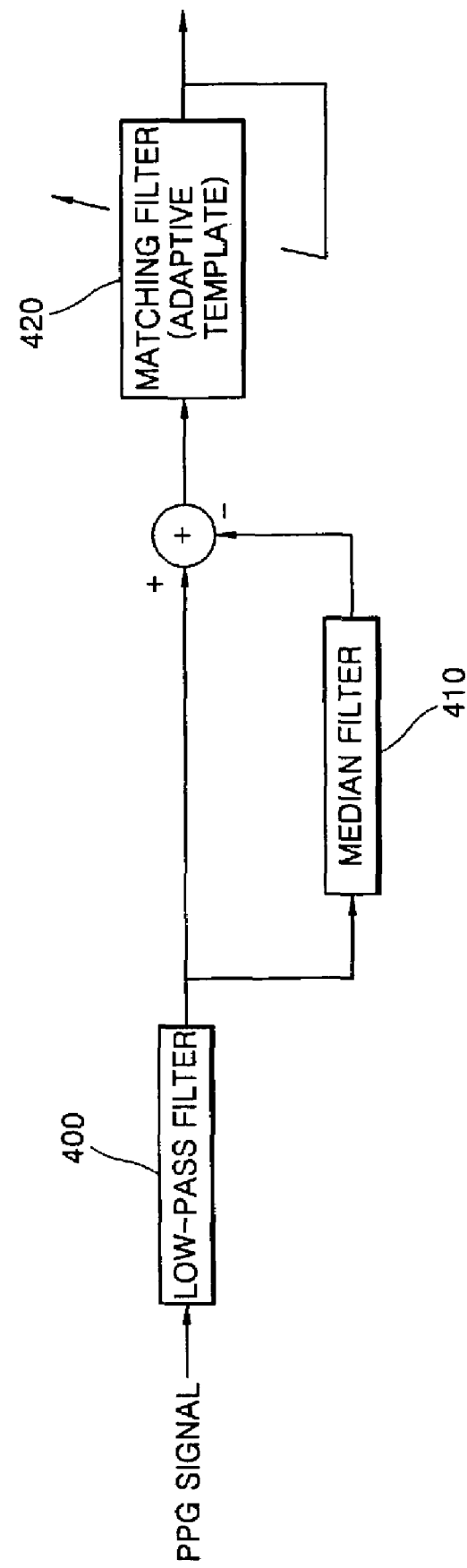
FIG. 4B is a block diagram of an example of a PPG signal processor.

An example of the PPG described above is shown in FIG. 4A. FIG. 4B is a block diagram of an example of a PPG signal processor according to the present disclosure.

Referring to FIG. 4B, a PPG signal is passed through a low-pass filter 400 to remove high-frequency noise. The PPG signal output from the low-pass filter 400 is passed through a medial filter 410 to estimate a very low frequency baseline variation. The very low frequency baseline variation is subtracted from the low-pass filtered PPG signal in order to obtain a waveform, from which the very low frequency baseline variation and direct current and high frequency components are removed. The resulting signal is passed through a matching filter to read PPG peaks. Heart rate and heart rate variability are measured using the PPG peaks.

Figure 5A:
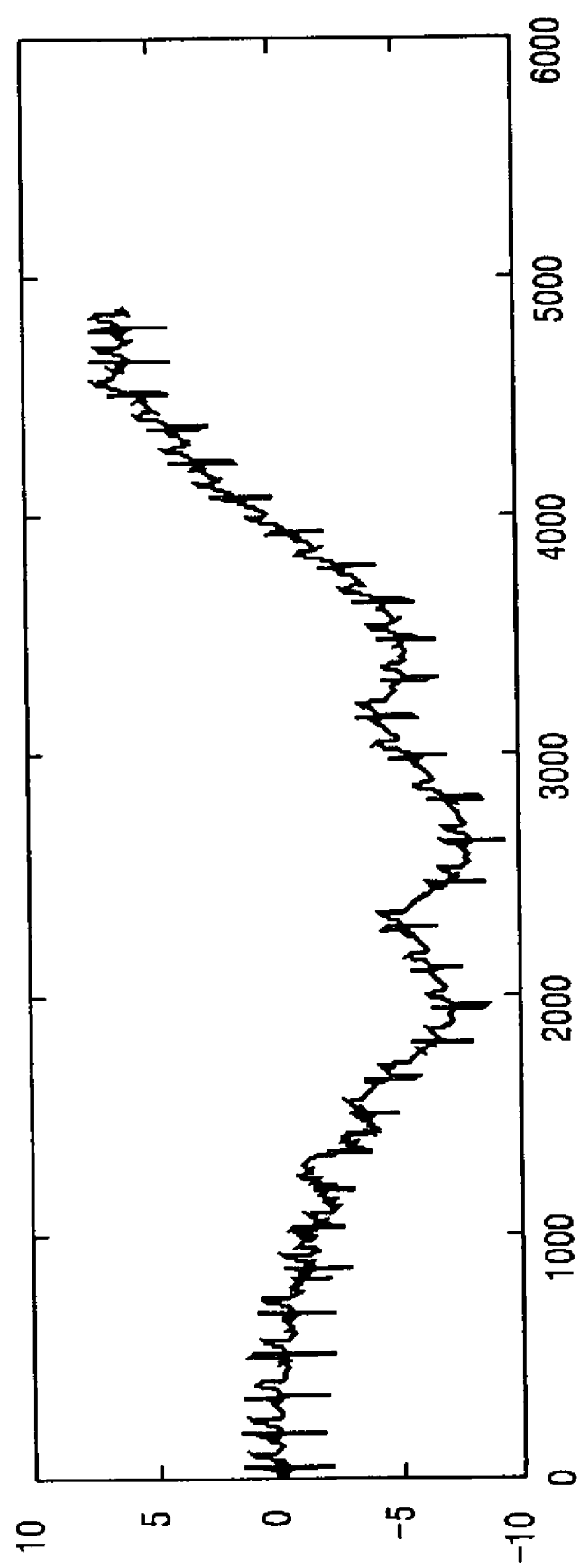
FIG. 5A shows an electrocardiogram (ECG) waveform of an animal measured using a two-electrode or three-electrode method.
Figure 5B:
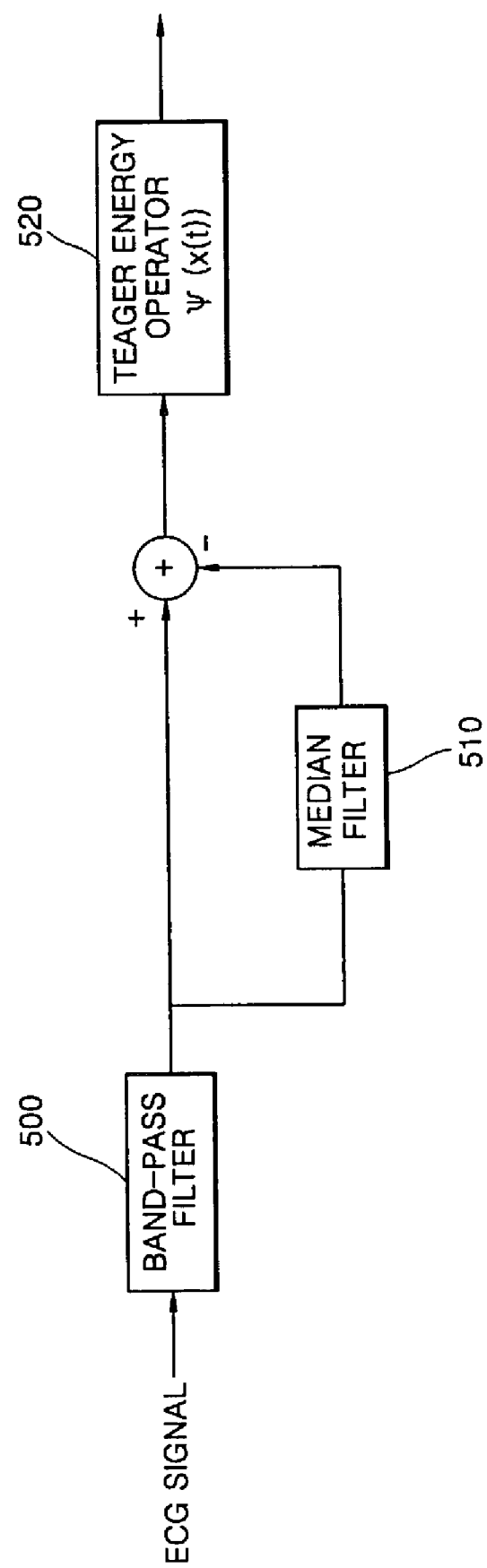
FIGS. 5B through 5D are block diagrams of an embodiment of an ECG signal processor according to the present disclosure for detecting R-peaks of the ECG.
Figure 5C:
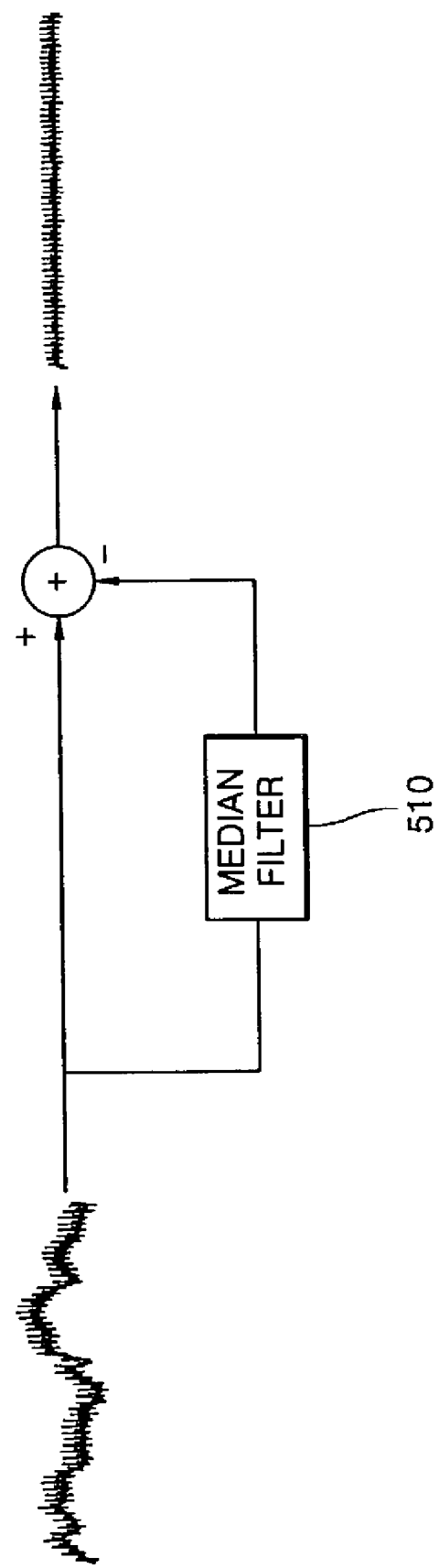
Figure 5D:
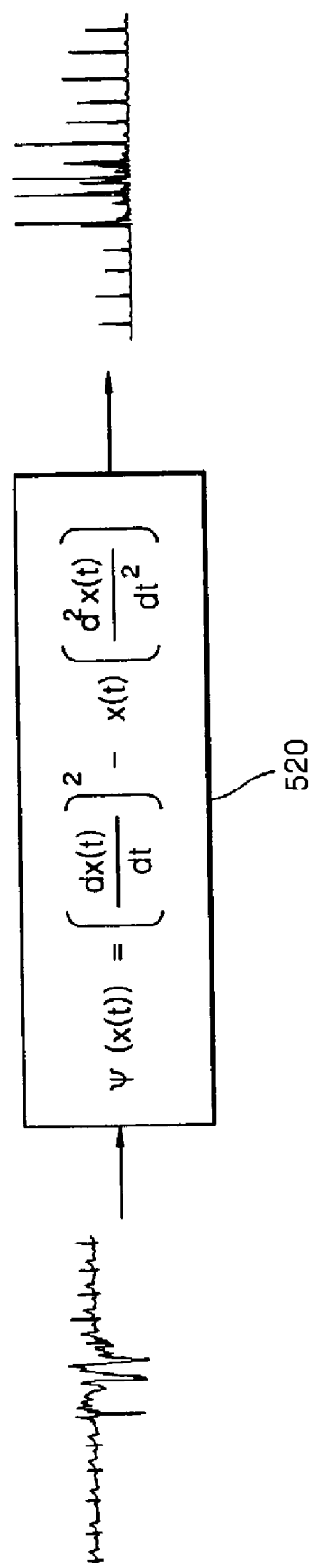

FIG. 5A shows an ECG of an animal obtained using the two-electrode or three-electrode method. FIGS. 5B through 5D are block diagrams of an embodiment of an ECG signal processor according to the present disclosure, for detecting R-peaks from an ECG signal in order to determine the instant the heart beat.

In particular, FIG. 5B is an overall block diagram of the ECG signal processor, which performs a time series analysis of heart rate variability by processing an ECG signal. The ECG signal of FIG. 5A is passed through a band-pass filter 500 to remove background noise that does not belong to the QRS complex frequency band. The ECG signal from the band-pass filter 500 is passed through a median filter 510 to estimate a baseline variation. The baseline variation is subtracted from the band-pass filtered ECG signal in order to obtain a waveform from which the baseline variation and background noise are removed. FIG. 5C illustrates an input and an output of the median filter 510 so as to visualize the function of the media filter 510.

The signal output from the median filter 510 is applied to a Teager energy operator (TEO) 520 ("Neural spike sorting under nearly 0 dB signal-to-noise ratio using non-linear energy operation and artificial neural network classifier, Kyung Hwan Kim et al., IEEE Transactions on Biomedical Engineering, 2000) in order to detect R-peaks in which the amplitude and frequency abruptly rise and to measure time-series heart rate variability from the intervals of the R-peaks.

FIG. 5D illustrates an input, an output, and the operating function of the TEO 520 to explain the function of the TEO 520.

After detecting heart beats, time-series heart rate variability is measured through smoothing and down-sampling. This process is widely known to those of ordinary skill in the art and can be easily implemented by such people ("An efficient algorithm for spectral analysis of heart rate variability", R. D. Berger et al., IEEE Trans. Biomed. Eng., Vol. 33).

Figure 6:
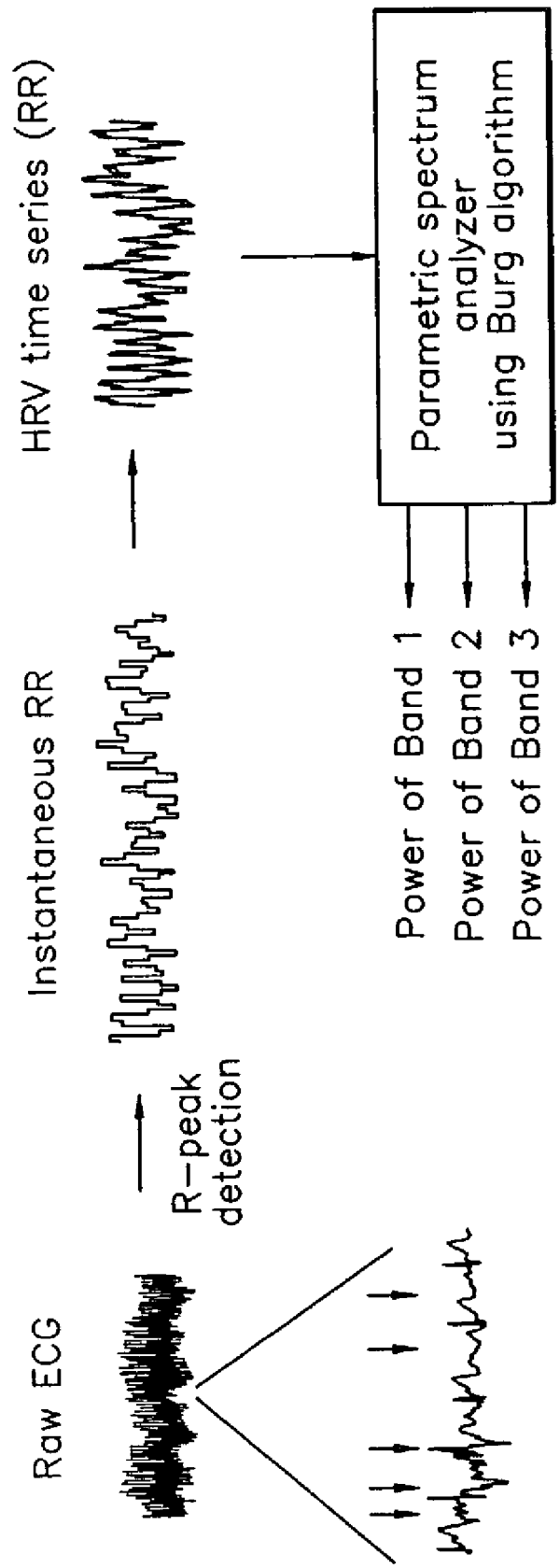
FIG. 6 illustrates a process for calculating the power of particular frequency bands from time-series heart rate variability through autoregressive modelling using the Burg algorithm.

FIG. 6 illustrates a process for calculating the power of particular frequency bands from the time-series heart rate variability through autoregressive modelling using the Burg algorithm.

Through the autoregressive modelling using the Burg algorithm, the power of three frequency bands, a very low frequency (VLF) band of 0.0043-0.04 Hz, a low frequency (LF) band of 0.04-0.15 Hz, and a high frequency (HF) band of 0.15-0.4 Hz, are calculated from the time-series heart rate variability. The autoregressive modelling using the Burg algorithm is described in "Statistical Digital Signal Processing and Modelling", M. Hayes, Wiley, 1996.

In addition to the frequency domain features, time-domain features, such as the mean heart rate in a time interval or its standard deviation, are used as feature vectors indicating the biological condition of an animal. When the standard deviation is calculated, the heart rates within 10% of the maximum and minimum heart rates are eliminated so as to reduce misdetection of the R-peaks.

Figure 7A:
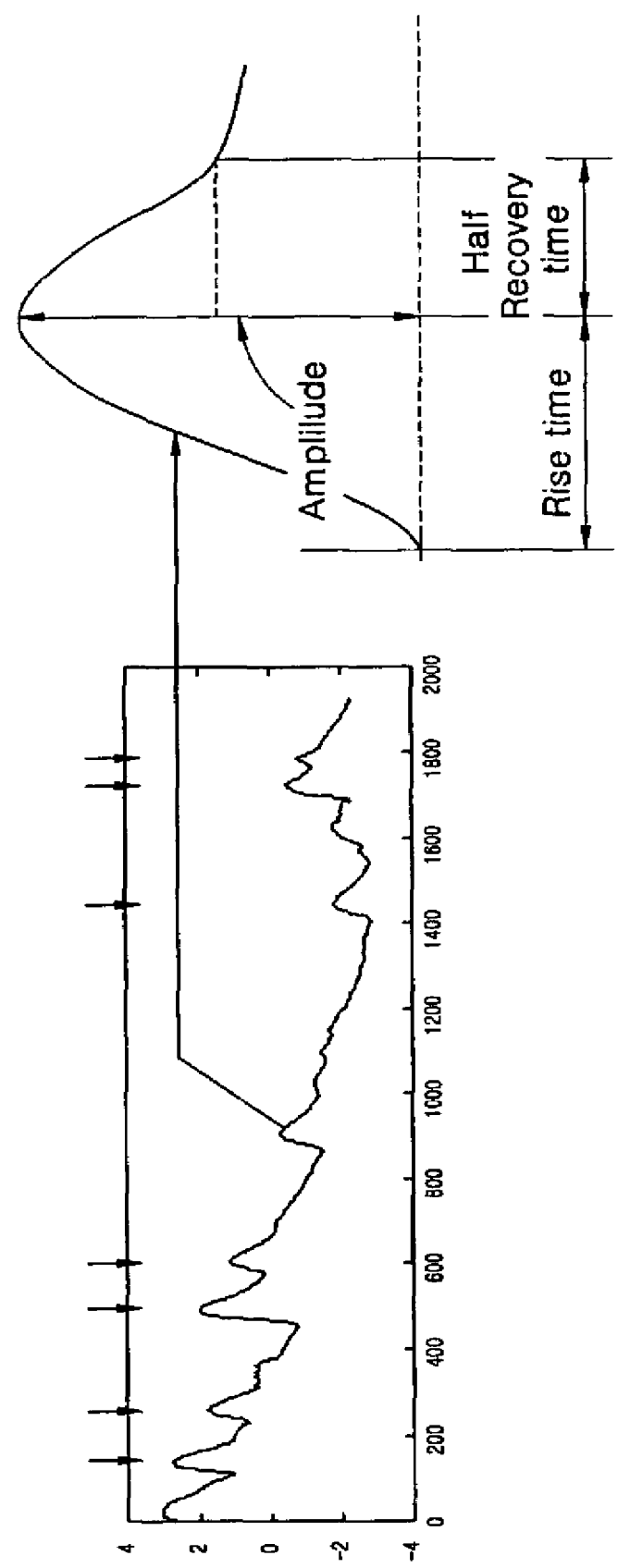
FIG. 7A shows an example of an electrodermal activity (EDA) waveform obtained using the sensor module of FIG. 3A or 3B as the biological signal detection unit attached to the animal's body.

FIG. 7A shows an example of an EDA waveform obtained using the sensor module of FIG. 3A or 3B. The EDA waveform can be obtained by measuring the voltage difference between two metal electrodes of the sensor module of FIG. 3A or 3B after flowing a small amount of current across the metal electrodes. The EDA waveform reflects the activity of the glandulae sudoriferae that is controlled by the sympathetic nervous system and is mostly influenced by the degree of stimulation and stress.

Parameters reflecting the EDA features in FIG. 7A include the mean level of the EDA waveform, the amplitude and duration of feature waveforms, which are called "skin conductance responses (SCRs)", the frequency of SCRs in a unit period of time, etc. In order to extract those parameters, the SCRs are detected as follows.

Figure 7B:
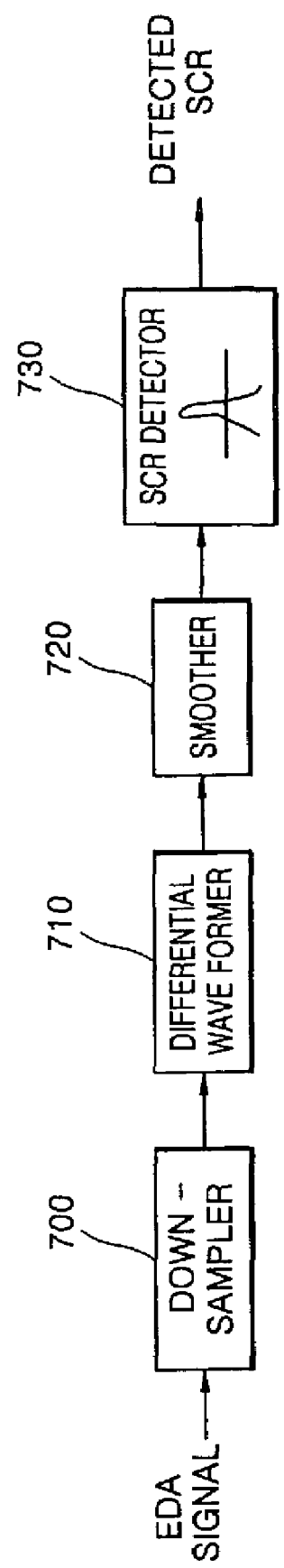
FIG. 7B is a block diagram of an embodiment of an apparatus for detecting skin conductance responses, which can be used in extracting feature vectors, from an EDA signal according to the present disclosure.

FIG. 7B is a block diagram of an embodiment of an apparatus for detecting SCRs, which can be used in extracting feature vectors, from an EDA signal, according to the present disclosure. Initially, the input EDA waveform has a sampling rate of about 256 Hz. The sampling rate is lowered to $\{\text{fraction}(1/10)\}$-12 by a down-sampler 700. A differential waveform is obtained by a differential wave former 710. In a smoother 720, the differential waveform is smoothened by convolution with a Bartlett window, for example, having a length of 20 ("Statistical Digital Signal Processing and Modelling", M. Hayes, Wiley, 1996). In a SCR detector 730, two points of the smoothened waveform that intersects a threshold level are taken as the start and end points of an SCR.

Skin temperature (SKT) can be measured using a small thermal sensor, such as a semiconductor thermal sensor, a thermistor, etc. The mean, maximum, and minimum temperatures in a predetermined time interval, and preferably, the mean and maximum temperature, are used as major parameters.

The feature vector extraction unit 202 extracts feature waveforms indicative of the animal's biological condition using the sensed biological signals and extracts feature vectors reflecting the animal's current emotional condition related with the autonomic nervous system, as described above.

According to the present disclosure, 9 feature vectors, including the mean heart rate and its standard deviation (from which the heart rates within 10% of the upper and lower limits are excluded), the VLF, LF, and HF components of the heart rate variability, the frequency and mean amplitude of SCRs of the EDA, and the mean and maximum skin temperatures, are extracted.

The biological condition analysis unit 250 receives the feature vectors extracted by the feature vector extraction unit 230 using the biological signals, which indicate the condition of the autonomic nervous system, and compares the feature vectors with reference vector data previously stored in the biological information database 240 so as to select maximum likelihood biological information, which is most likely to match the animal's current condition, among a predetermined number of biological information categories stored in the biological information database 240. The reference vector data refers to the predetermined number of biological information categories for different kinds of animals that reflect their behaviors, needs, and emotions in various biological conditions. As a result, the physical and mental conditions of animals can be measured.

Extracting reference information on the animal's emotional conditions from the biological information database 240 and determining which reference information best reflects the feature vectors extracted by the biological condition analysis unit 250 using the biological signals can be achieved using the following principles.

If the feature vectors reflecting particular emotional conditions form one probability distribution in multi-dimensional space and the probability density function for each of the emotional conditions is known, a statically optimal classifier can be configured using the Bayes rule (Pattern Classification, 2nd Ed., R. O. Duda, P. E. Hart, and D. G. Stock, 2000, Wiley).

However, it is practically impossible to obtain accurate probability density functions. For this reason, a multiplayer perceptron, a Parzen window classifier implemented based on significant rules that are equivalent to the Bayes rule, through learning of a limited number of data, etc. are commonly used. However, this type of classifier is highly likely to operate inaccurately when unlearned new data are used. In other words, those classifiers show poor generalization performance. An attempt has been made to eliminate this drawback by Fisher projection, which provides the maximum amount of separation between clusters, among other linear projection techniques. As a result of projecting data distribution of higher dimensions into two dimensions, as can be expected, the variance within each cluster was great, and the degree of overlap of clusters was high. In other words, the sizes of the feature vector clusters were very large, and feature vector clusters of different conditions overlapped considerably. Therefore, the classifier using a limited number of learned data is highly likely to operate inaccurately.

According to the present disclosure, support vector machine (SVM) known to provide better generalization performance than the two above-described methods is used as a classifier. The SVM is implemented based on the fact that linear mapping into higher dimensions can increase the probability of linear separation and using a Vapnik statistical learning theory-based method for configuring a linear classifier having optimal generalization performance.

Parameters that define the learning rule in the classifier are determined by establishing a higher dimensional linear classifier equation capable of minimizing classification errors and maximizing generalization performance using given learned data. Based on the solutions of this equation, a linear mapping method for mapping the original dimension into a higher dimension can be realized.

A detailed description on the SVM will not be provided here (V. Vanik, "An Overview of Statistical Leaning Theory", IEEE Transactions on neural network, Vol. 10, No. 5, pp. 988-999, 1999).

Figure 8:
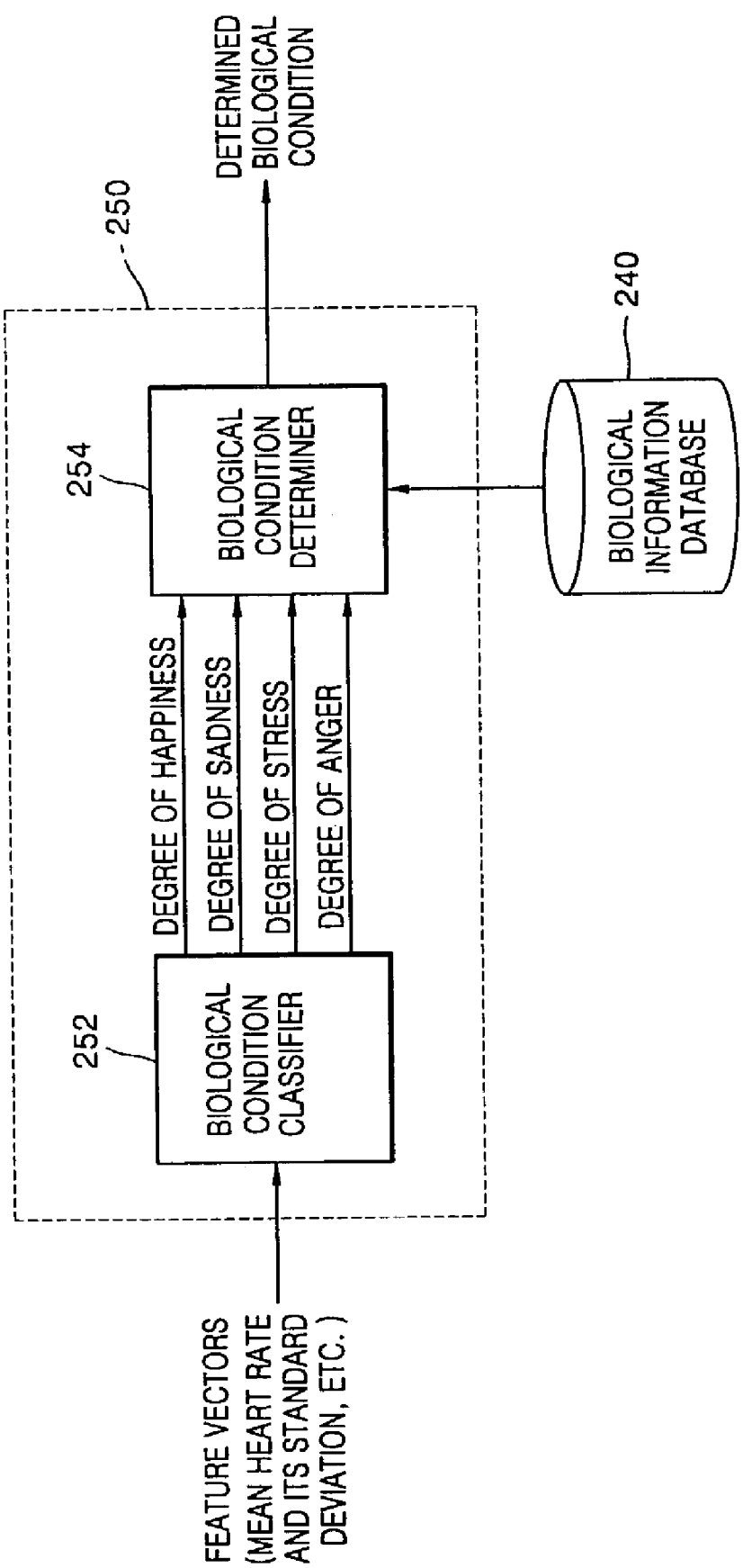
FIG. 8 is a detailed block diagram of a biological condition analysis unit according to the present disclosure.

FIG. 8 is a detailed block diagram of the biological condition analysis unit 250 according to the present disclosure. A biological condition classifier 252 classifies the feature vectors extracted by the feature vector extraction unit 230, according to biological condition categories using the above describe SVM, for example, degree of happiness, degree of sadness, degree of stress, degree of anger, degree of tension, and degree of fear, etc. In a biological condition determiner 254, the biological condition categories of the animal are compared with the reference vector data on the basic biological conditions of animals stored in the biological information database 240 in order to determine the final biological condition of the animal, and the result of the determination is output.

Figure 9A:
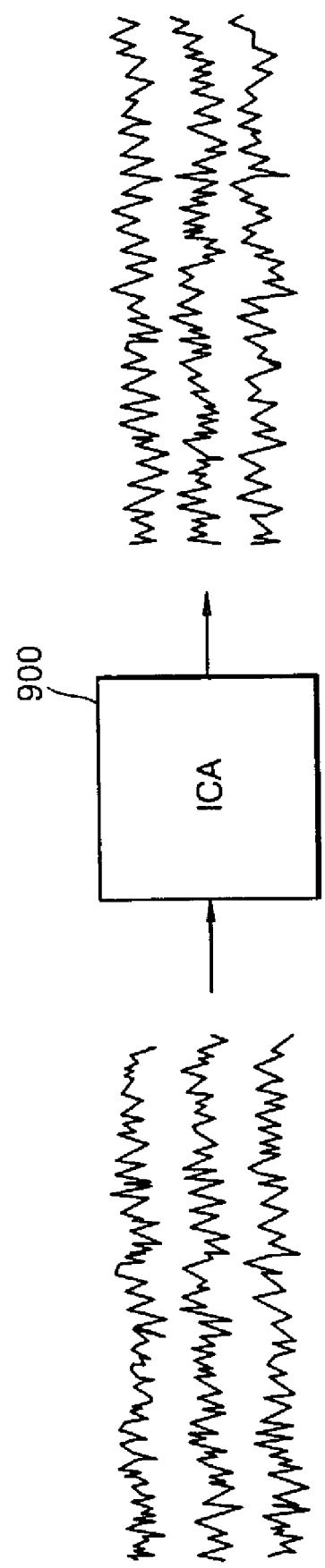
FIG. 9A shows raw electrogastrographic (EGG) waveforms and EGG waveforms after pre-processing by independent component analysis (ICA)
Figure 9B:
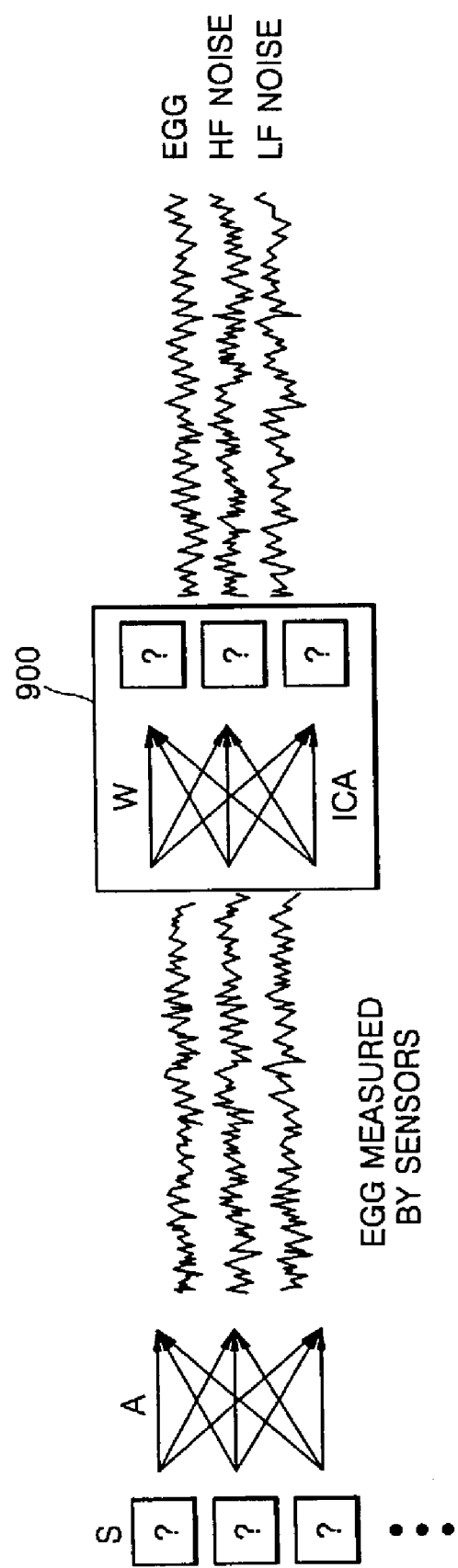
FIG. 9B illustrates EGG waveforms sensed from unknown sources by sensors of the biological signal detection unit, which includes noise, and EGG waveforms from which the noise is removed by ICA.

FIG. 9A shows an EGG waveform of an animal and an EGG waveform of the animal after pre-processing by independent component analysis (ICA). FIG. 9B illustrates EGG waveforms taken from unknown sources by sensors on the biological signal detection unit 200, which include noise, and EGG waveforms from which noise has been removed by an independent component analyser (ICA) 900.

To measure how hungry an animal is, an EGG is taken from which parameters indicative of the electrical activity of gastric myoblasts can be extracted. To this end, the wearable sensor module as shown in FIG. 3B is used. The electrodes are arranged in the sensor module such as to contact appropriate positions of the animal's abdomen so as to detect electrical signals.

According to the present disclosure, since the animal is forced to wear the sensor module serving as the biological signal detection unit 200 so that the electrical signals can be continuously detected, a large motion artifact due to the motion of the animal can result. To eliminate this problem, it is preferable to further perform a pre-process of blind source separation in the ICA so as to separate a motion waveform, an instrumental noise waveform, and a target EGG signal, after measuring an EGG using a multi-channel electrode array in the sensor module corresponding to the biological signal detection unit 200. A detailed description on ICA can be found in "Independent Component Analysis", Aapo Hyvarinen, Wiley, 2001).

Figure 10A:
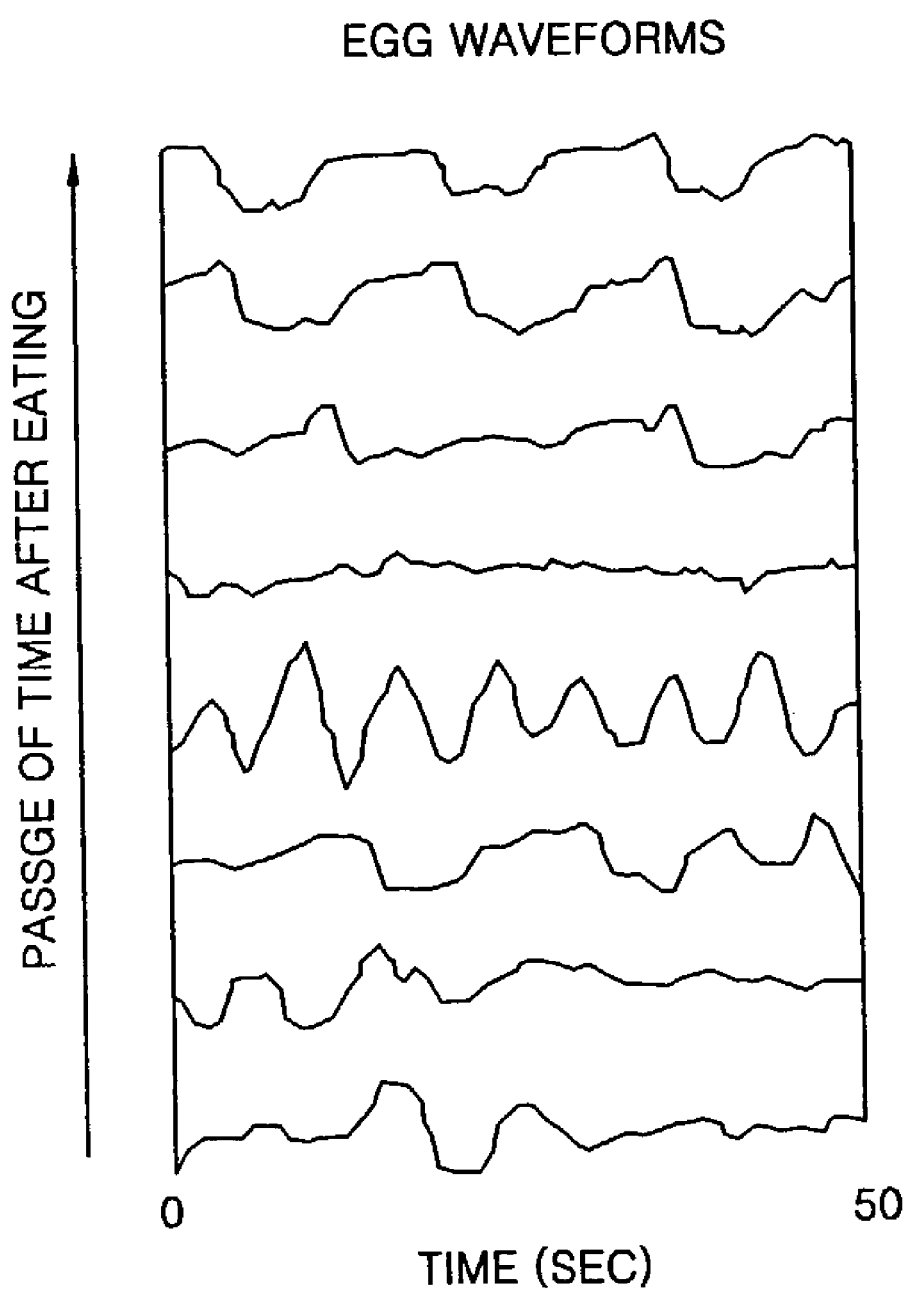
FIG. 10A shows EGG waveforms after pre-processing.
Figure 10B:
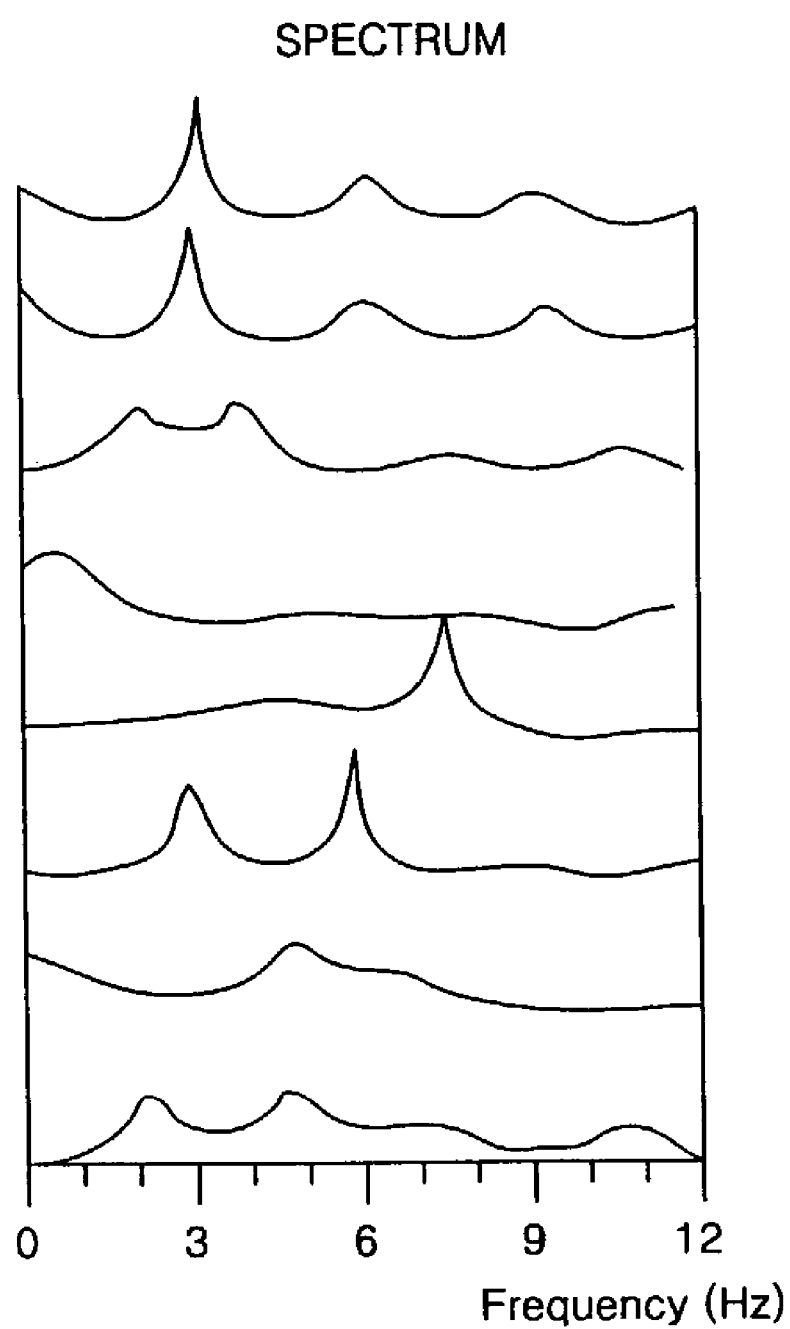
FIG. 10B shows a time-varying spectrum obtained using the EGG waveforms of FIG. 1A.

FIG. 10A shows EGG waveforms after pre-processing, and FIG. 10B shows a time-varying spectrum obtained using the EGG waveforms of FIG. 1A. The EGG waveforms after post-processing as shown in FIG. 9 are cut to, for example, a length of about 50 seconds, as shown in FIG. 10A, and overlapped by 10 seconds in order to obtain the time-varying spectrum of FIG. 10B.

It is preferable that the time-varying spectrum be obtained using a Burg algorithm-based autoregressive model.

J. Chen et al. reported EGG spectrum variations with respect to the amount of time passed after eating in IEEE Transactions on Biomedical Engineering, 1993, under the title of "Spectral Analysis of Episodic Rhythmic Variations in the Cutaneous Electrogastrogram". Based on this report, the gastric condition of the animal can be measured using the EGG spectrum.

The feature vector extraction unit 230 measures EGG spectra several times before and after eating using a particular pet, classifies the level of hunger into one of many levels, and generates 2-dimensional feature vector data which is constituted of spectral peaks and widths. The values of the spectral peaks and widths can be obtained using the time-varying spectra of FIG. 10B. The feature vector extraction unit 230.

The biological condition analysis unit 250 compares the feature vector related to the level of hunger with the reference vector stored in the biological information database 240 and determines the current gastric condition of the animal corresponding to the level of hunger.

Figure 11:
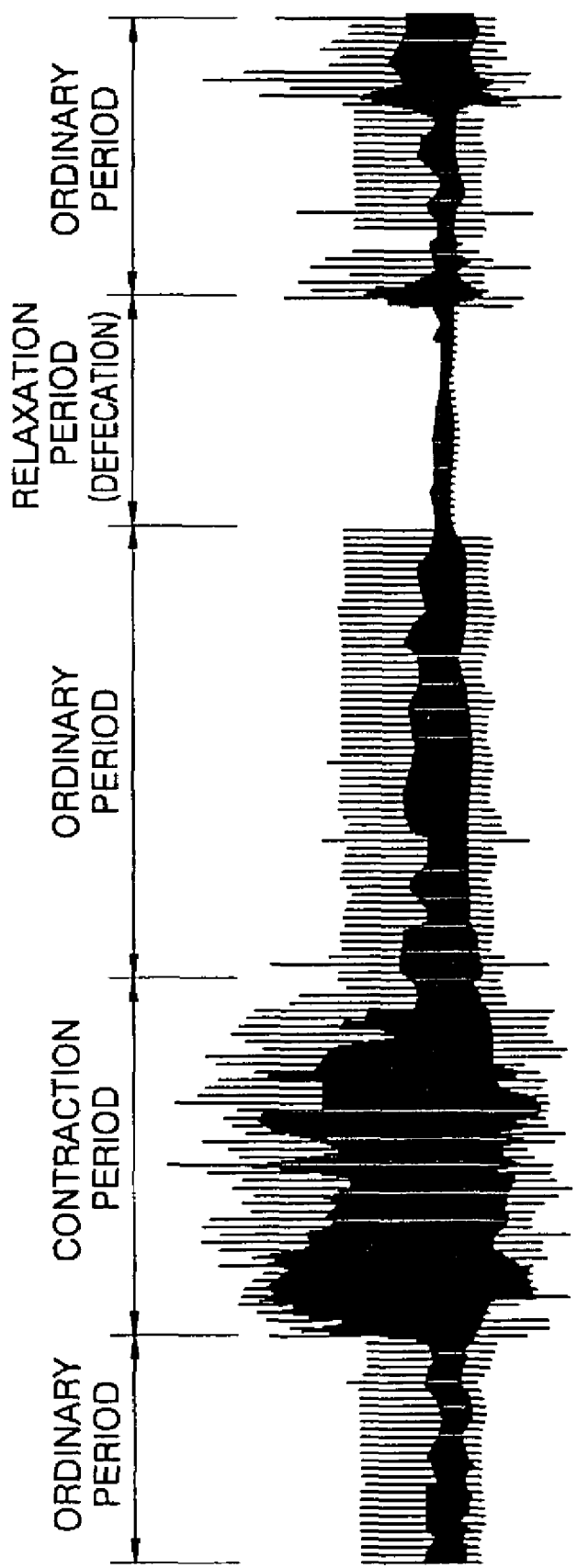
FIG. 11 shows an example of an electromyographic (EMG) waveform related to bowel movement.

FIG. 11 shows an example of an EMG waveform related to a bowel movement. In order to determine whether the animal needs to have a bowel movement, an EMG of the anal muscles is measured by contacting an electrode/sensor of the sensor module to the anal muscles, and the amplitude of the EMG signal is compared with reference data for the normal condition. As a result, it can be determined whether the animal needs to have a bowel movement from the contraction of the anal muscles. The bowels are emptied after a predetermined ordinary period following the contraction period. The condition of the bowels can be measured from an EMG taken of the excretive organic muscles.

In the ordinary period, a basal electrical activity is detected. As the sphincter ani are contracted to control the bowl movement need, the electrical activity increases. When the sphincter ani are strained to allow bowel movement, the sphincter ani are relaxed, and the electrical activity decreases.

The magnitude of EMG signals can be easily measured by those of ordinary skill in the art, using an envelope detection method including zero-clipping and smoothening processes.

The levels of tension and fear can be determined from the heart rate variability, EDA, and skin temperature. One of ordinary skill in the art can easily determine the levels of tension and fear using the method according to the present disclosure.

After the determination of the biological condition of the animal by the biological condition analysis unit 250 is completed, it is preferable that the animal's owner be informed of the result of the determination through the wireless transmission unit 260.

Alternatively, the biological signals of the animal detected in step 100 or the biological condition of the animal determined in step 120 can be transmitted to an expert, such as a veterinarian, via the wireless transmission unit 260 for special examination. In this case, the result of the special examination can be fed back to the owner through wireless transmission.

Figure 12:
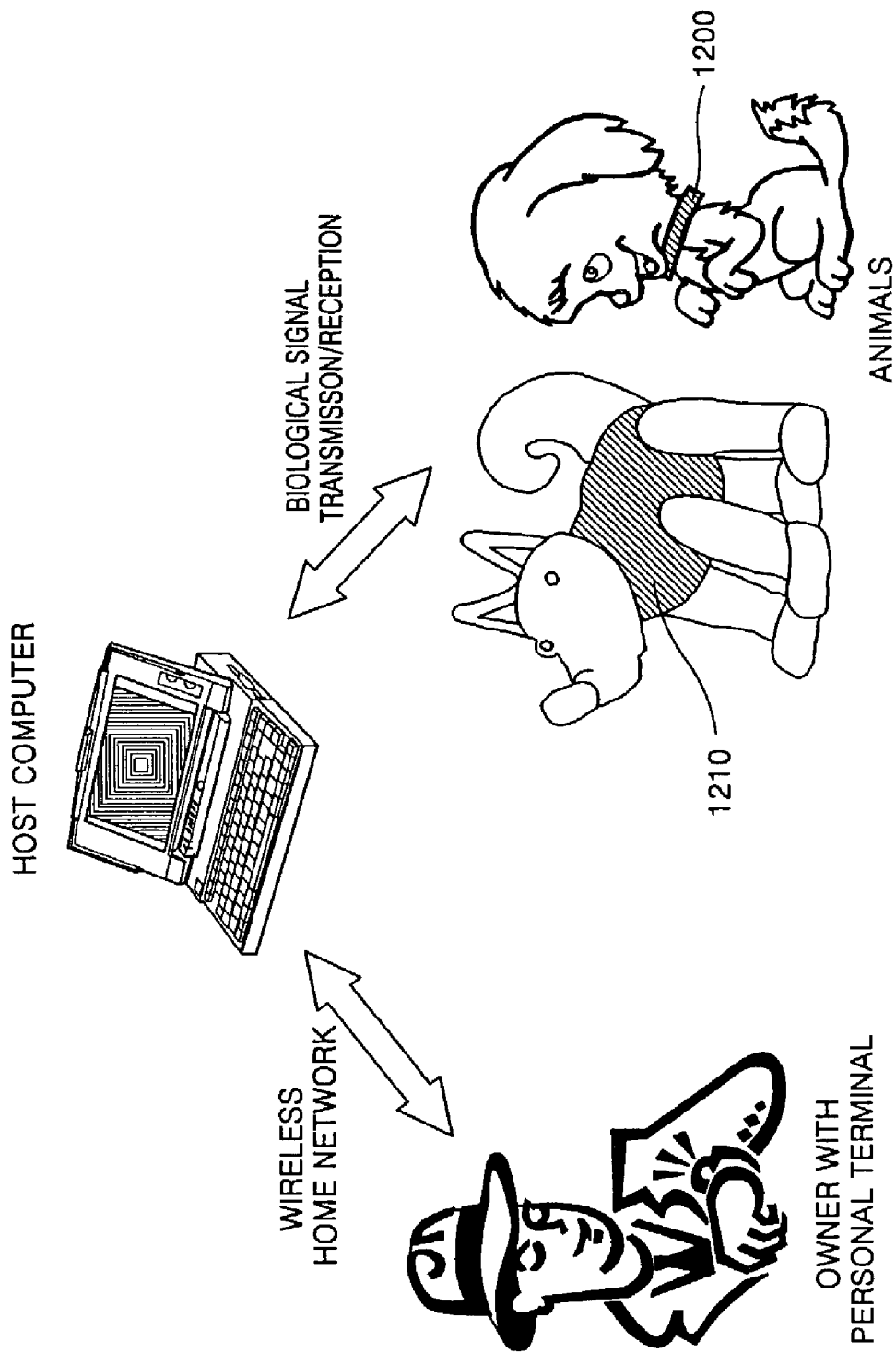
FIG. 12 illustrates a system for measuring the biological condition of an animal, which is constructed of a collar type sensor module or a wearable sensor module and contacts the animal's body, a host computer which determines the biological condition of the animal by receiving and processing biological signals, and a wireless personal terminal which receives the result of the animal's determined biological condition.

Accordingly, the owner can communicate with his/her pet by being informed of the biological condition of the pet:

FIG. 12 illustrates a system for measuring the biological condition of an animal, which is constructed of a collar type sensor module 1200 or a wearable sensor module 1210, which contacts the animal's body, a host computer which determines the biological condition of the animal by receiving and processing biological signals, and a wireless personal terminal which receives the result of the animal's determined biological condition.

The collar type sensor module 1200 put around the neck of a pet, which serves as the biological signal detection unit 200, may include a sensor for measuring PPG from the caroticum, a small semiconductor thermal sensor for sensing the skin temperature, and two metal electrodes for measuring EDA. The sensor for measuring the PPG can be constructed with a photodiode or a light emitting diode (LED). The collar type sensor module 1200 includes a basic signal processing circuit for amplification and filtering and a circuit for wireless transmission.

The PPG, the skin temperature, and the EDA measured and transmitted by the collar type sensor module 1200 are transmitted to a computer via a wireless receiver and a home network. The biological signals transmitted via the wireless receiver can be transmitted to the computer via an interface, for example, RS-232C.

In the computer which receives the biological signals, the feature vector extraction unit 230, the biological information database 240, the biological condition analysis unit 250, etc. are implemented using software. From these elements, it can be determined whether the response of the animal's autonomic nervous system is joy, sorrow, impatience, or anger. The determined information is transmitted from the computer to a terminal that is carried by the owner, such as a personal data assistant (PDA) or watch-like terminal, and displayed as an icon or text. Alternatively, when the biological condition of the animal is determined to be poor, the result of the determination and the detected biological signals can be immediately transmitted to a previously assigned expert, such as a veterinarian, for diagnostic purposes.

When the wearable sensor module 1210 is used as the biological signal detection unit 200 so as to measure the condition of the animal, an ECG, EGG, and anal EMG can be additionally measured. As a result, in addition to the above-listed emotions, the biological needs of the animals, such as hunger or bowel movement, can be determined.

While the present invention has been particularly shown and described with reference to preferred embodiments thereof, it will be understood by those of ordinary skill in the art that various changes in form and details may be made to the present invention without departing from the spirit and scope of the present invention as defined by the appended claims. The above-described embodiments are provided for illustrative purposes so that the present invention will be thorough and complete and are not intended to limit the spirit and scope of the present invention.

It will be appreciated by one of ordinary skill in the art that each of the steps in the animal's condition determination method according to the present disclosure can be variously embedded using software by general programming or using hardware.

Some steps of the method according to the present disclosure may be embodied as computer-readable program code units embedded in a computer-usable medium, including but not limited to storage media such as magnetic storage media (e.g., ROM's, floppy disks, hard disks, etc.), optically-readable media (e.g., CD-ROMs, DVDs, etc.), and carrier waves (e.g., transmission over the Internet). The computer-readable medium has embodied thereon computer-readable program codes that can be run on a number of computer systems connected via a network.

According to the present disclosure, biological signals of an animal are obtained from the skin temperature, ECG, PPG, EDA, EMG, and EGG measured using a biological signal detection unit attached to the animal skin, and feature vectors, including the mean heart rate in the PPG and its standard deviation, the VLF, LF, and HF components of heat rate variability, the frequency and mean amplitude of skin conductance responses in the EDA, and the mean and maximum skin temperatures, can be extracted from the biological signals. The feature vectors are compared with reference vectors stored in a predetermined database, which reflect the behaviors, needs, and emotions of different animals for various biological conditions, to determine the biological condition of the animal, for example, whether the animal feels hunger or fear, how much the animal is stressed, or whether the animal needs to have a bowel movement. As a result, although human languages are not used, an animal's owner or handler can determine the animal's biological condition through communication with his/her animal, thereby providing an efficient pet breeding method.

When a biological signal-based system is applied to people for non-medical purposes, one inconvenience that is apparent is that sensors must always be attached to the object. However, this inconvenience does not seem serious for the pets.

According to the present disclosure, an animal's owner can reliably measure the emotional condition or some biological needs of his/her pets through instrumental communication, not through human languages. In addition, the animal's owner can monitor the condition of his/her pet outdoors using a home network, a wireless phone, or a PDA, which have become increasingly popular.

What is claimed is:

1. A method for determining the biological condition of a non-human animal by acquiring and analyzing a biological signal, the method comprising:
   (a) acquiring a predetermined biological signal using a biological signal detection unit which is adapted to be attached to the non-human animal;
   (b) extracting a predetermined feature vector from the acquired predetermined biological signal, wherein the feature vectors include any one or any combination of the mean heart rate of the photoplethysmogram and its standard deviation, the very low frequency, low frequency, and high frequency components of heart rate variability of the non-human animal; and
   (c) analyzing and determining the biological condition of the non-human animal, including emotions and needs of the non-human animal, from the predetermined feature vector.

2. A method for determining the biological condition of an animal by acquiring and analyzing biological signals, the method comprising: (a) acquiring biological signals from skin temperature, a photoplethysmogram (PPG), an electrocardiogram (ECG), electrodermal activity (EDA), an electromyogram (EMG), and an electrogastrogram (EGG) using a biological signal detection unit which is adapted to be attached to the animal's skin; (b) extracting feature vectors from the acquired biological signals, the feature vectors including any one or any combination of the mean heart rate of the photoplethysmogram and its standard deviation, the very low frequency, low frequency, and high frequency components of heart rate variability, the frequency and mean amplitude of skin conductance responses which are obtainable from the electrodermal activity, and the mean and maximum skin temperatures; and (c) analyzing and determining the biological condition, including needs and emotions, of the animal as to whether or not the animal feels hunger or fear, how much the animal is stressed, or whether or not the animal needs to have a bowel movement, using a support vector machine which has learned reference vectors, which reflect the behaviors, needs, and emotions of different kinds of animals for various biological conditions and are stored in a predetermined database.

3. The method of claim 2, wherein extracting the mean heart rate as one of the feature vectors in step (b) from the photoplethysmogram, which is acquired as a biological signal in step (a), comprises: (b1) low-pass filtering the photoplethysmogram to remove high frequency noise; (b2) median-filtering an output signal in step (b1), from which the high frequency noise is removed, to estimate a baseline variation to a very low frequency; (b3) subtracting an output signal in step (b2) from the output signal in step (b1) to obtain a waveform from which the baseline variation and direct current and high frequency components are removed; and (b4) matching-filtering an output signal in step (b3) to obtain the location of peaks of the photoplethysmogram and measure the heart rate and heart rate variability.

4. The method of claim 2, wherein extracting the very low frequency, low frequency, and high frequency components of heart rate variability as feature vectors in step (b) from the electrocardiogram, which is acquired as a biological signal in step (a), comprises: (b1') bandpass-filtering the electrocardiogram to remove background noise which does not belong to the electrocardiographic frequency band; (b2') median-filtering an output signal in step (b1') from which the background noise is removed to estimate a baseline variation; (b3') subtracting an output signal in step (b1') from the output signal in step (b2') to obtain a waveform from which the baseline variation and noise which does not belong to the frequency band are removed; (b4') applying an output signal in step (b3') to a Teager energy operator to detect R-peaks in which the amplitude and frequency abruptly rise; (b5') measuring time-series heart rate variability from the intervals of the R-peaks; and (b6') calculating the power of particular frequency bands from the measured time-series heart rate variability through autoregressive modelling using the Burg algorithm.

5. The method of claim 4, wherein when the standard deviation of heart rates is calculated as one of the feature vectors in step (b), the heart rates within a predetermined range of the maximum and minimum heart rates are excluded.

6. The method of claim 2, wherein extracting the frequency and amplitude of skin conductance responses as feature vectors in step (b) from the electrodermal activity, which is acquired as a biological signal in step (a), comprises: (b1") down-sampling an input electrodermal activity waveform; (b2") obtaining a differential waveform from an output waveform in step (b1"); (b3") smoothing the differential waveform in step (b2") by convolution with a Bartlett window having a predetermined length; and (b4") determining two points of the smoothened waveform that have a predetermined threshold level as the start and end points of a skin conductance response, respectively.

7. The method of claim 2, wherein in step (c), whether or not the animal feels hunger is determined using a feature vector extracted from the electrogastrogram acquired as a biological in step (a).

8. The method of claim 7, wherein in step (b), blind source separation is performed on the electrogastrogram acquired in step (a) by independent component analysis in order to remove noise from an animal's motion and an instrumental noise waveform, and the resulting electrogastrogram is cut to a time length ad overlapped by a predetermined time period to obtain a time-varying spectrum through autoregressive modelling using the Burg algorithm as a feature vector indicating the degree of hunger of the animal, and a step (c), based on a plurality of electrogastrograms measured in step (b), the degree of hunger is classified into a predetermined number of levels, 2-dimensional feature vector data which are constituted of spectral peaks and widths for each level are generated, and the degree of hunger of the animal is determined by comparing the 2-dimensional feature vector with reference vector stored in a predetermined support vector machine.

9. The method of claim 2, wherein in step (c), whether or not the animal feels fear and how much the animal is stressed are determined using the feature vectors extracted from the electrocardiogram, electrodermal activity, and skin temperature acquired in step (a).

10. The method of claim 2, wherein in step (c), whether or not the animal needs to have a bowel movement is determined using a feature vector extracted from the electromyogram acquired in step (a) of anal muscles.

11. The method of claim 2, further comprising (d) informing an animal's owner of the biological condition, including needs and emotions, of the animal via a predetermined communication unit.

12. The method of claim 2, further comprising: (e) transmitting the biological signals of the animal acquired to step (a) and/or the biological condition, including needs and emotions, of the animal determined in step (c) to an animal's handler via a predetermined communication unit; and (f) the animal's handler informing an animal's owner of the results of a diagnosis performed using the biological signals and/or the biological condition of the animal via a predetermined communication unit.

13. An apparatus for measuring the biological condition of a non-human anima; by acquiring and analysing biological signals, the apparatus comprising:
   a biological signal section unit which is adapted to be attached to the non-human animal's skin and detects a biological signal of the non-human animal; and
   a condition analysis unit which determines the biological condition, including needs and emotions, of the non-human animal by comparing a predetermined feature vector including any one or any combination of the mean heart rate of the photoplethysmogram and its standard deviation, the very low frequency, low frequency, and high frequency components of heart rate variability of the animal with a feature vector extracted by analyzing the biological signal detected by the biological signal detection unit.

14. The apparatus of claim 13, further comprising a transmission unit which wirelessly transmits the biological condition, including needs and emotions, of the animal that has been analyzed by the condition analysis unit to a person.

15. The apparatus of claim 13, further comprising a transmission unit which wirelessly transmits the biological signal(s) detected by the biological signal detection unit or the biological condition determined by the condition analysis unit to a person.

16. An apparatus for measuring the biological condition of an animal by acquiring biological signals, the apparatus comprising:
   a biological signal detection unit including a plurality of sensors and electrodes, which is adapted to be attached to the animal's skin and detects biological signals from skin temperature, and electrocardiogram (ECG), a photoplethysmogram (PPG), electrodermal activity (EDA), an electromyogram (EMG), and an electrogastrogram (EGG);
   a feature vector extraction unit which extracts feature vectors from the biological signals detected by the biological signal detection unit, the feature vectors including the mean heart rate of the photoplethysmogram and its standard deviation, the very low frequency, low frequency, and high frequency components of heart rate variability, the frequency and mean amplitude of skin conductance responses, and the mean and maximum skin temperatures;
   a biological information database which stores reference vectors reflecting the behaviors, needs, and emotions of different kinds of animals for various biological conditions; and
   a biological condition analysis unit which compares the feature vectors extracted by the feature vector extraction unit with reference vectors of the biological information database and determines the biological condition, including needs and emotions, of the animals as to whether or not the animal feels hunger or fear, how much the animal is stressed, or whether or not the animal needs to have a bowel movement.

17. The apparatus of claim 16, further comprising a transmission unit which wirelessly transmits the biological condition, including needs and emotions, of the animal that has been analyzed by the biological condition analysis unit to a person.

18. The apparatus of claim 16, further comprising a transmission unit which wirelessly transmits the biological signal(s) detected by the biological signal detection unit or the biological condition determined by the biological condition analysis unit to a person.

19. A method for determining the biological condition of an animal by acquiring and analyzing a biological signal, the method comprising:
   (a) acquiring a predetermined biological signal using a biological signal detection unit which is adapted to be attached to the animal;
   (b) extracting a predetermined feature vector, elected from a plurality of feature vectors corresponding to different kinds of animals, from the acquired predetermined biological signal, wherein the feature vectors include any one or any combination of the mean heart rate of the photoplethysmogram and its standard deviation, the very low frequency, low frequency, and high frequency components of heart rate variability of the different kinds of animals; and
   (c) analyzing and determining the biological condition of the animal, including emotions and needs of the animal, from the predetermined feature vector.

20. An apparatus for measuring the biological condition of an animal by acquiring and analysing biological signals, the apparatus comprising:
   a biological signal detection unit which is adapted to be attached to the animal's skin and detects a biological signal of the animal;
   and a condition analysis unit which determines the biological condition, including needs and emotions, of the animal by comparing a predetermined feature vector including any one or any combination of the mean heart rate of the photoplethysmogram and its standard deviation, the very low frequency, low frequency, and high frequency components of heart rate variability of the animal, selected from a plurality of feature vectors corresponding to different kinds of animals, with a feature vector extracted by analyzing the biological signal detected by the biological signal detection unit.

* * * * *